US012742188B2

(12) United States Patent
Xie et al.

(10) Patent No.: US 12,742,188 B2

(45) Date of Patent: Sep. 22, 2026

(54) **APPLICATION OF TRANSPORT CARRIER GENE WHICH IMPROVES L-TRYPTOPHAN PRODUCTION EFFICIENCY IN *ESCHERICHIA COLI***

(71) Applicants: Ningxia Eppen Biotech Co., LTD, Ningxia (CN); Tianjin University of Science & Technology, Tianjin (CN)

(72) Inventors: Xixian Xie, Tianjin (CN); Bo Xiong, Tianjin (CN); Chunguang Zhao, Ningxia (CN); Xiaowei Guo, Ningxia (CN); Jiaxuan Men, Tianjin (CN); Aiying Wei, Ningxia (CN)

(73) Assignees: NINGXIA EPPEN BIOTECH CO., LTD, Ningxia (CN); TIANJIN UNIVERSITY OF SCIENCE & TECHNOLOGY, Tianjin (CN)

( * ) Notice: Subject to any disclaimer, the term of this patent is extended or adjusted under 35 U.S.C. 154(b) by 1247 days.

(21) Appl. No.: 17/638,689

(22) PCT Filed: Oct. 23, 2019

(86) PCT No.: PCT/CN2019/112848

§ 371 (c)(1), (2) Date: Feb. 25, 2022

(87) PCT Pub. No.: WO2021/042460

PCT Pub. Date: Mar. 11, 2021

(65) Prior Publication Data

US 2022/0411835 A1 Dec. 29, 2022

(30) Foreign Application Priority Data

Sep. 3, 2019 (CN) ........................ 201910828913.5

(51) Int. Cl.

*C12P 13/22* (2006.01)
*C07K 14/32* (2006.01)

(Continued)

(52) U.S. Cl.

CPC ........... *C12P 13/227* (2013.01); *C07K 14/32* (2013.01); *C12N 1/20* (2013.01); *C12N 1/205* (2021.05);

(Continued)

(58) Field of Classification Search

CPC ... C12P 13/227; C12N 15/70; C12N 2310/20; C12N 1/205; C12R 2001/19; C07K 14/32

See application file for complete search history.

(56) References Cited

FOREIGN PATENT DOCUMENTS

| | | |
|---|---|---|
| CN | 108753860 A | 11/2018 |
| CN | 109370966 A | 2/2019 |

(Continued)

OTHER PUBLICATIONS

Bjerre et al. Biotechnol Lett (2017) 39:289-295 (Year: 2017).*

(Continued)

*Primary Examiner* — Kimberly Chong
*Assistant Examiner* — Africa M Mcleod
(74) *Attorney, Agent, or Firm* — HAUPTMAN HAM, LLP

(57) ABSTRACT

A transport protein coding gene, and a method for efficient production of L-tryptophan by a strain containing the gene. Specifically, by heterologous expression of ywkB gene from *Bacillus subtilis* on the genome of *Escherichia coli*, L-tryptophan production efficiency of the strain can be improved. Performing shake flask fermentation with the strain can accumulate 15.2 g/L of L-tryptophan within 24 h, which is 35% higher than a control strain.

4 Claims, 3 Drawing Sheets

Specification includes a Sequence Listing.

(51) Int. Cl.

| | |
|---|---|
| ***C12N 1/20*** | (2026.01) |
| ***C12N 1/205*** | (2026.01) |
| ***C12N 9/22*** | (2006.01) |
| ***C12N 15/11*** | (2006.01) |
| ***C12N 15/70*** | (2006.01) |
| ***C12R 1/19*** | (2006.01) |

(52) U.S. Cl.

CPC ................ *C12N 9/22* (2013.01); *C12N 15/11* (2013.01); *C12N 15/70* (2013.01); *C12N 2310/20* (2017.05); *C12N 2800/80* (2013.01); *C12R 2001/19* (2021.05)

(56) References Cited

FOREIGN PATENT DOCUMENTS

| | | | |
|---|---|---|---|
| CN | 109486737 | A | 3/2019 |
| CN | 110643559 | A | 1/2020 |
| EP | 0994190 | A2 | 4/2000 |
| EP | 1016710 | A2 | 7/2000 |
| JP | 2005278405 | A | 10/2005 |
| WO | 9723597 | A2 | 7/1997 |
| WO | 2015050276 | A1 | 4/2015 |

OTHER PUBLICATIONS

Belbahri, Lassaad, et al. "Comparative Genomics of Bacillus Amyloliquefaciens Strains Reveals a Core Genome with Traits for Habitat Adaptation and a Secondary Metabolites Rich Accessory Genome." Frontiers in Microbiology, vol. 8, Aug. 3, 2017, https://doi.org/10.3389/fmicb.2017.01438. (Year: 2017).*

Goodall, Emily C. A., et al. "The Essential Genome of *Escherichia coli* K-12." MBio, vol. 9, No. 1, Feb. 20, 2018, https://doi.org/10.1128/mbio.02096-17. (Year: 2018).*

Charbonnier, Teddy, et al. "Molecular and Physiological Logics of the Pyruvate-Induced Response of a Novel Transporter in Bacillus Subtilis." MBio, vol. 8, No. 5, Oct. 4, 2017, https://doi.org/10.1128/mbio.00976-17. Accessed Oct. 14, 2024. (Year: 2017).*

International Search Report in Corresponding International Application No. PCT/CN2019/112848, mailed May 28, 2020; 10 pgs.

Liu, Lina et al; L-Tryptophan Production in *Escherichia coli* Improved by Weakening the Pta-AckA Pathway; PLOS One; vol. 11, No. 6, Jun. 27, 2016; 16 pages.

Niu, Hao et al; "Metabolic engineering for improving L-tryptophan production in *Escherichia coli*"; Journal of Industrial Microbiology & Biotechnology; vol. 46, 2019; pp. 55-65.

Zhao, Zhijun et al; "Effect of mufti-gene knockout of L-tryptophan transport system on L-tryptophan production in *Escherichia coli*"; Chinese Journal of Biotechnology; Dec. 25, 2011; vol. 27, No. 12; pp. 1765-1772.

Li, Jing et al.; "Effect of engineering of L-tryptophan transport system on L-tryptophan reproduction in *Escherichia coli*"; Science and Technology of Food Industry; vol. 38, No. 15, 2017; pp. 157-163.

Liu, Qian et al.; "Modification of tryptophan transport system and its impact on production of L-tryptophan in *Escherichia coli*"; Bioresource Technology; vol. 114; 2012; pp. 549-554.

Gu, Pengfei et al.; "Knocking out analysis of tryptophan permeases in *Escherichia coli* for improving L-tryptophan production"; Appl. Microbiol Biotechnol; vol. 97; 2013; pp. 6677-6683.

Bjerre, Karin et al.; "Development of Bacillus subtilis mutants to produce tryptophan in pigs"; Biotechnol Lett, vol. 39, 2017, pp. 289-295.

* cited by examiner

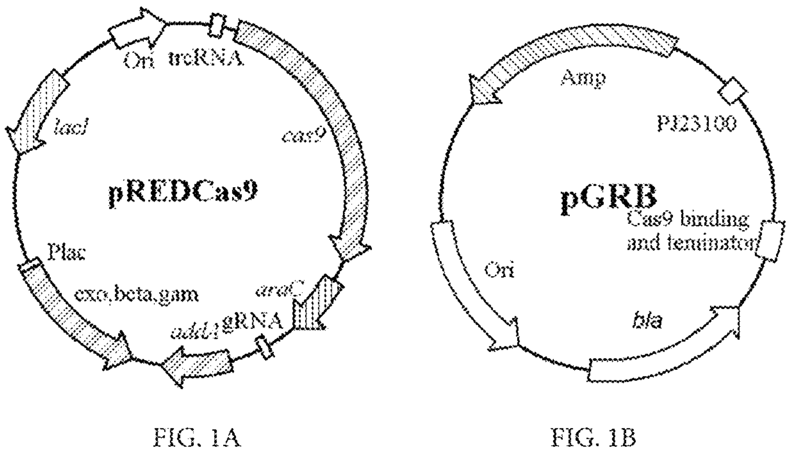
FIG. 1A
FIG. 1B
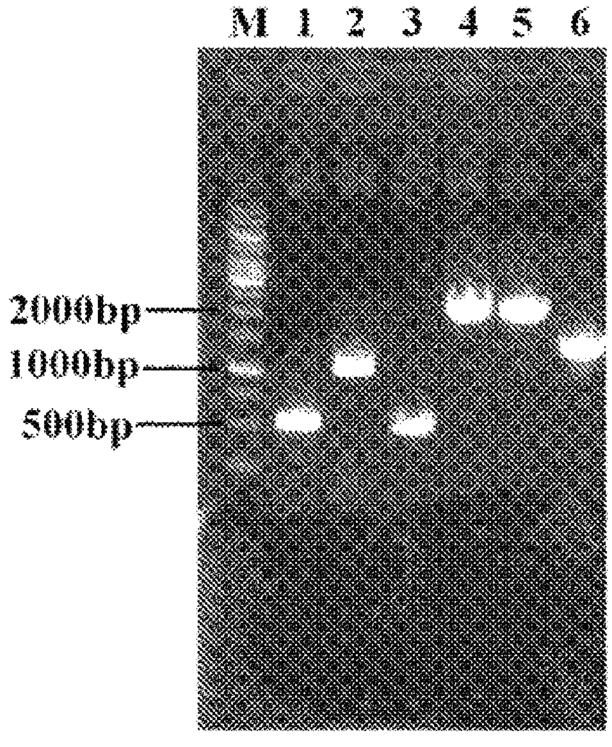
FIG. 2

APPLICATION OF TRANSPORT CARRIER GENE WHICH IMPROVES L-TRYPTOPHAN PRODUCTION EFFICIENCY IN *ESCHERICHIA COLI*

RELATED APPLICATIONS

This application is a U.S. National Phase of International Application Number PCT/CN2019/112848 filed Oct. 23, 2019, and claims priority from Patent Application No. 201910828913.5, filed with the China National Intellectual Property Administration on Sep. 3, 2019, and titled "APPLICATION OF TRANSPORT CARRIER GENE WHICH IMPROVES L-TRYPTOPHAN PRODUCTION EFFICIENCY IN *ESCHERICHIA COLI*", the disclosure of which is hereby incorporated by reference herein in its entirety.

INCORPORATION BY REFERENCE

The sequence listing provided in the file entitled C6351-070_Amended_SQL.txt, which is an ASCII text file that was created on Apr. 1, 2022, and which comprises 6,145 bytes, is hereby incorporated by reference in its entirety.

TECHNICAL FIELD

The present invention relates to metabolic engineering and biotechnology, in particular to a metabolite transport carrier gene derived from *Bacillus subtilis*, which can effectively improve the amino acid production efficiency of an engineered L-tryptophan-producing *Escherichia coli* strain.

BACKGROUND OF THE INVENTION

Tryptophan, as an amino acid that plays an important role in regulating the growth and development of organisms and has good pharmacological effects such as anti-depression and promoting sleep, plays an important role in food, medicine, animal feed and other industries. With the further study of this amino acid, its application will be wider, which is bound to make the market demand for tryptophan rise sharply. Therefore, seeking for a more efficient and cheap tryptophan production process gradually attracts people's attention. At present, its production methods include chemical synthesis method, enzymatic reaction method and direct microbiological fermentation method. The direct fermentation method is a method for directly producing L-tryptophan through fermentation with low-cost raw materials such as glucose as substrates. This method has the advantages of easy manipulation, low cost, high yield, short cycle, and low environmental pollution. However, the research on the internal environment of microorganisms and the equilibrium relationship between various metabolic pathways is still not thorough, resulting in low yields of microbiological fermentation methods. Moreover, as for the synthesis of L-tryptophan, the synthesis pathway is longer and requires more precursors. Therefore, in order to realize the further increase of yield, it is necessary to systematically engineer the microbial metabolic network by means of metabolic engineering.

At present, metabolic engineering technology is widely used in the improvement of industrial strains. Metabolic engineering mainly uses technologies such as DNA recombination and CRISPR/Cas9-mediated gene editing to optimize pathway enzymes directly involved in amino acid synthesis, key rate-limiting enzymes, and regulatory factors not directly involved in amino acid synthesis. In addition to these strategies, enhancing the target product transport capacity of strains can also effectively improve the amino acid production efficiency.

A variety of amino acid-secreting protein-encoding genes have been reported, all of which can effectively improve the production capacity of strains. For example, increasing the expression of the lysine-secreting gene lysE can improve the production capacity of lysine-producing bacteria of the genus *Corynebacterium* (WO9723597A2). Increasing the expression of the rhtB gene increases bacterial tolerance to L-homoserine (European Patent Application EP994190A2). Additional copies of the rhtC gene increase the yields of L-homoserine, L-threonine and L-leucine (European Patent Application EP1013765A1). Additional copies of the yahN, yeaS, yfiK and yggA genes increase the yields of L-glutamate, L-lysine, L-threonine, L-alanine etc. (European Patent Application EP 1016710A2).

The transport protein most widely reported in aromatic amino acid-producing bacteria is encoded by *E. coli*'s own gene, yddG. Among them, Vera Doroshenko et al. used *Escherichia coli* MG1655 as the starting strain, and expressed different intensities of yddG gene by plasmid or genome integration. In the test tube fermentation experiments, the accumulation of L-tryptophan was 0.6 μg/mL, and the accumulation of L-phenylalanine was 30,000 μg/mL. Liu Shuangping er al. introduced the yddG gene into an *E. coli* host strain in the form of plasmid through genetic engineering. Fermentation experiments proved that the L-phenylalanine extracellular transport capacity of the strain containing yddG gene was improved, and the final L-phenylalanine yield reached 62 g/L. In another study, the tryptophan-producing *Escherichia coli* strain SV164 (pGH5) was used as the parental strain, and the yddG gene controlled by a strong promoter was introduced into the cells to obtain the SV164PL-yddG (pGH5) strain. The strain was subjected to shaking culture at 37° C. for 48 h in a 20×200 mm test tube, and the final L-tryptophan yield was 4.17 g/L, which was about 12% higher than that of the starting strain.

From the above cases, it can be found that overexpression of yddG gene can enhance the tolerance of engineered strains to aromatic amino acids, but the membrane proteins encoded by this gene have large differences in affinity for different aromatic amino acids, and the transport effect is not good. This gene is derived from *Escherichia coli*, so it is easily subject to the self-regulation of the bacteria and cannot exert an efficient transport function. This gene is difficult to meet the requirements of industrial production.

SUMMARY OF THE INVENTION

The purpose of the present invention is to improve the production efficiency of an L-tryptophan-producing strain and utilize the strain to produce L-tryptophan. In order to achieve the above-mentioned purpose, the present invention improves the production efficiency of L-tryptophan by a host strain by introducing the encoding gene ywkB (Gene ID: 936875) of the metabolite transporter derived from *Bacillus subtilis* subsp into the host strain. ywkB is a membrane protein-encoding gene, which encodes a putative metabolite transporter and belongs to the auxin efflux carrier family (TC 2.A.69), it does not directly participate in the synthesis of L-tryptophan, but when the gene is introduced into the L-tryptophan-producing strain, it can effectively reduce the concentration of the intracellular end product and relieve the feedback inhibition of the end product on the metabolic pathway enzymes, and make more carbon flow to the target amino acid synthesis pathway, and ultimately improves the product yield.

The first technical solution provided by the present invention is: a genetically engineered bacterial strain for producing L-tryptophan, wherein a bacterial host strain is modified with ywkB gene, and the obtained genetically engineered bacterial strain has the activity of producing a higher yield of L-tryptophan than the bacterial host strain.

According to the genetically engineered bacterial strain of the present invention, the ywkB gene is from *Bacillus subtilis*, and the modification is to modify the yeep pseudogene locus with the ywkB gene.

According to the genetically engineered bacterial strain of the present invention, the bacterial host strain is a bacterial host strain capable of producing L-tryptophan, and the specific bacterial species is not particularly limited, as long as it has the ability to produce L-tryptophan or it can obtain this ability; for example, the bacterial host strain can be a strain of prokaryotic bacteria capable of producing L-tryptophan, such as a strain of gram-negative bacteria capable of producing L-tryptophan; further, the bacterial host strain is an *Escherichia coli* strain capable of producing L-tryptophan; for example, the bacterial host strain is L-tryptophan-producing *E. coli* strain TRP 03 (this strain is obtained by genetically modifying the starting strain *Escherichia coli* W3110, and is the same strain as *E. coli* TRP 03 (CN 108753860 A)).

According to the genetically engineered bacterial strain of the present invention, the ywkB gene has a nucleotide sequence encoding the following polypeptide sequence:

(A) a protein comprising the amino acid sequence shown in SEQ ID NO: 2 in the sequence listing;

(B) a protein which comprises the amino acid sequence obtained by performing deletion, substitution and/or addition of one or more amino acid residues on the amino acid sequence shown in SEQ ID NO: 2 in the sequence listing and still has the ability to improve the production of L-tryptophan and L-tryptophan structural analogs (such as 5-hydroxytryptophan, etc.) by the strain;

(C) a protein which has at least 85%, preferably at least 90%, more preferably at least 95%, more preferably at least 96%, 97%, 98%, 99% identity with the amino acid sequence shown in SEQ ID NO: 2, derives from *Bacillus subtilis* and functions as a metabolite transporter.

According to the genetically engineered bacterial strain of the present invention, the step of "a bacterial host strain is modified with ywkB gene" refers to introducing the gene into the bacterial host strain.

The method of introducing the encoding gene into the bacterial host strain includes but is not limited to genetic engineering means familiar to those skilled in the art, such as introducing the target gene into the bacterial host strain by means of homologous recombination; or introducing the target gene into the bacterial host strain by means of expression nucleic acid constructs and specifically the expression nucleic acid construct can be a common plasmid that is familiar to those skilled in the art and can be expressed in a prokaryotic host; or the target gene is inserted into the chromatin of the host by means of gene editing.

According to the genetically engineered bacterial strain of the present invention, wherein the ywkB gene is under the control of a strong promoter, for example, the strong promoter is a BBa_j23101 promoter or a BBa_j23106 promoter.

Specifically, the modification of the present invention is to use the *Escherichia coli* CRISPR/Cas9 gene editing technology to introduce the transporter encoding gene ywkB into *E. coli* TRP 03, and further, is to integrate the gene controlled by the BBa_j23106 promoter into the yeep pseudogene locus.

The nucleotide sequence of the ywkB gene is shown in SEQ ID NO: 1.

The amino acid sequence of the ywkB gene is shown in SEQ ID NO: 2.

The nucleotide sequence of the BBa_j23106 promoter is shown in SEQ ID NO: 3.

The second technical solution provided by the present invention is: a method for constructing a genetically engineered bacterial strain that produces L-tryptophan, in which ywkB gene is integrated into a bacterial host strain to obtain a genetically engineered bacterial strain having the activity of producing a higher yield of L-tryptophan than the bacterial host strain.

According to the construction method of the present invention, wherein the integrating step is performed by modifying the yeep pseudogene locus with the ywkB gene, for example, the integrating is performed by means of CRISPR-Cas9 gene editing.

According to the construction method of the present invention, the tryptophan-producing *E. coli* strain TRP 03 preserved in the laboratory of Tianjin University of Science and Technology is used as the starting strain, and the ywkB gene is integrated, and the specific steps are as follows:

(1) synthesizing ywkB integrated gene fragment: constructing upstream and downstream homologous arm fragments of the yeep pseudogene, ywkB gene fragment and BBa_j23106 promoter sequence, the ywkB integrated gene fragment comprising the upstream homologous arm of the yeep gene, the downstream homologous arm of the yeep gene, the BBa_j23106 promoter fragment and the ywkB gene fragment;

(2) expressing the ywkB integrated gene fragment in *E. coli* TRP 03 using CRISPR/Cas9 technology.

According to the construction method of the present invention, wherein the ywkB gene sequence is a nucleotide sequence encoding the following polypeptide sequence:

(A) a protein comprising the amino acid sequence shown in SEQ ID NO: 2 in the sequence listing;

(B) a protein which comprises the amino acid sequence obtained by performing deletion, substitution and/or addition of one or more amino acid residues on the amino acid sequence shown in SEQ ID NO: 2 in the sequence listing and still has the ability to improve the production of L-tryptophan and L-tryptophan structural analogs (such as 5-hydroxytryptophan, etc.) by the strain;

(C) a protein which has at least 85%, preferably at least 90%, more preferably at least 95%, more preferably at least 96%, 97%, 98%, 99% identity with the amino acid sequence shown in SEQ ID NO: 2, derives from *Bacillus subtilis* and functions as a metabolite transporter.

The third technical solution provided by the present invention is: a genetically engineered bacterial strain obtained by the above-mentioned method for constructing a genetically engineered bacterial strain that produces L-tryptophan.

The fourth technical solution provided by the present invention is: a method for producing L-tryptophan, which comprises the step of fermenting the genetically engineered bacterial strain in the first solution of the present invention or the genetically engineered bacterial strain obtained by the method in the second solution to produce L-tryptophan.

According to the method for producing L-tryptophan of the present invention, it comprises the following steps:

1) activating the bacterial strain;
2) preparing a seed solution;
3) fermenting;

for example, wherein step 1) adopts slant culture: inoculating the bacterial strain preserved at −80° C. onto the activated slant using streak method, culturing at 37° C. for 12 h and passaged once;

step 2) adopts shake flask seed culture: scraping a ring of seeds on the slant with an inoculating loop and inoculating into a 500 mL conical flask containing 30 mL of seed medium, sealing the conical flask with nine layers of gauze, and culturing at 37° C. and 200 rpm for 8-10 h;

step 3) adopts shake flask fermentation culture: inoculating the seed culture at the concentration of 10-15% (v/v) into a 500 mL conical flask containing fermentation medium (final volume: 30 mL), sealing the conical flask with nine layers of gauze, culturing at 37° C. and 200 r/min in a shaking table, during the fermentation, adding ammonia water to maintain pH at 7.0-7.2; adding 60% (m/v) glucose solution to maintain fermentation (with phenol red as indicator, when the color of the fermentation broth no longer changes, it is regarded as lack of glucose, adding 1-2 mL of 60% (m/v) glucose solution to make the glucose concentration in the fermentation broth the initial value of 20-40 g/L); the fermentation period lasting for 22-26 h.

The present invention has the following advantages and beneficial effects:

The present invention introduces transport carrier-encoding gene ywkB derived from *Bacillus subtilis* into an engineered L-tryptophan-producing strain and significantly improves the yield of the target product. Since the gene comes from *Bacillus subtilis*, it will not be regulated by the engineering strain and function more easily. Therefore, the present invention has broad application prospects. The engineered L-tryptophan-producing strain containing the ywkB gene provided by the present invention can accumulate 15.2 g/L of L-tryptophan after 24 hours of shake flask fermentation, which is 35% higher than the starting strain, showing the potential for industrial production of L-tryptophan.

DESCRIPTION OF THE DRAWINGS

In FIGS. 1A and 1B, panel IA shows the pREDCas9 plasmid map and panel 1B shows the pGRB plasmid map.

FIG. 2 shows the electropherogram of BBa_j23106-ywkB gene fragment construction and verification, wherein M: 1 kb DNA marker; lane 1: upstream homologous arm; lane 2: ywkB; lane 3: downstream homologous arm; lane 4: overlapping fragment; lane 5: positive bacteria identification fragment; lane 6: control strain.

DETAILED DESCRIPTION OF THE INVENTION

Figure 3:
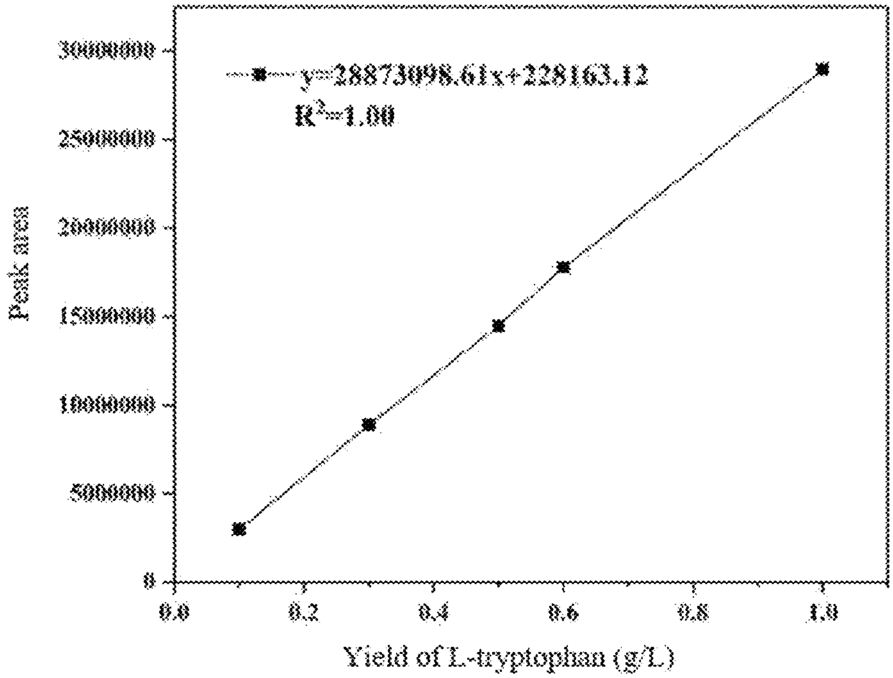
FIG. 3 shows the standard curve for L-tryptophan determination by HPLC.

Example 1: Construction of *E. coli* Strain TRP 05

1. Gene Editing Method

The gene editing method adopted in the present invention refers to literature "Li Y, Lin Z, Huang C, et al. Metabolic engineering of *Escherichia coli* using CRISPR-Cas9 mediated genome editing. Metabolic engineering, 2015, 31:13-21." and the maps of the two plasmids used in this method are shown in FIGS. 1A and 1B. Among them, the pREDCas9 vector carries an elimination system of the gRNA expression plasmid pGRB, a Red recombination system of λ phage and a Cas9 protein expression system, spectinomycin resistance (working concentration: 100 mg/L), cultured at 32° C.; the pGRB vector uses pUC18 as the backbone and contains a promoter J23100, a gRNA-Cas9 binding domain sequence and a terminator sequence, ampicillin resistance (working concentration: 100 mg/L), cultured at 37° C.

The specific steps of this method:

1.1 Construction of pGRB Plasmid

The purpose of constructing the plasmid pGRB is to transcribe the corresponding gRNA to form a complex with Cas9 protein, and recognize the target site of the target gene through base pairing and PAM to achieve the target DNA double-strand break. The pGRB plasmid was constructed by recombining a DNA fragment containing the target sequence with a linearized vector fragment.

1.1.1 Design of Target Sequence

CRISPR RGEN Tools was used to design the target sequence (PAM: 5'-NGG-3').

1.1.2 Preparation of DNA Fragment Containing Target Sequence

The primer 5'-linearized vector end sequence (15 bp)-restriction site-target sequence (without PAM sequence)-linearized vector end sequence (15 bp)-3' and its reverse complementary primer were designed, and a DNA fragment containing the target sequence was prepared by annealing of a single-stranded DNA. Reaction conditions: pre-denaturation at 95° C. for 5 min; annealing at 30-50° C. for 1 min. The annealing system was as follows:

Annealing system

| Reaction system | Volume (20 μL) |
| --- | --- |
| Primer | 10 μL |
| Reverse complementary primer | 10 μL |

1.1.3 Preparation of Linearized Vector

The linearization of the vector adopted the method of inverse PCR amplification.

1.1.4 Recombination Reaction

The recombination system is shown in the following table. The recombinases used were all enzymes of the ClonExpress® II One Step Cloning Kit series. Recombination conditions: 37° C., 30 min.

Recombination system

| Reaction system | Volume (10 μL) |
| --- | --- |
| 5 × CE II Buffer | 2 μL |
| Linearized clone vector | 0.5 μL |
| Inserted fragment clone vector | 0.5 μL |

-continued

| Recombination system | |
|---|---|
| Reaction system | Volume (10 μL) |
| Exnase ® II | 1 μL |
| $ddH_2O$ | 6 μL |

1.1.5 Transformation of Plasmid

Ten μL of the reaction solution were added to 100 mL of DH5α competent cells and mixed gently. The resulting mixture was cooled in an ice bath for 20 min, heated shock at 42° C. for 45-90 s, cooled immediately in an ice bath for 2-3 min, added with 900 μL of SOC, and recovered at 37° C. for 1 h. The mixture was centrifuged at 8,000 rpm for 2 min, part of the supernatant was discarded and the remaining 200 μL of the supernatant was used to resuspend the cells. The cells were then spread onto a plate containing 100 mg/L ampicillin, and the plate was placed upside down and cultured at 37° C. overnight. After single colonies were grown on the plate, positive recombinants were identified and picked by colony PCR.

1.1.6 Identification of Clones

The PCR-positive colonies were inoculated into LB medium containing 100 mg/L ampicillin for overnight culture, and the bacteria were preserved.

The plasmids were extracted and identified by enzyme digestion.

1.2 Preparation of Recombinant DNA Fragment

The recombinant fragment for knockout consists of the upstream and downstream homologous arms of the gene to be knocked out (upstream homologous arm-downstream homologous arm); the recombinant fragment for integration consists of the upstream and downstream homologous arms of the integration site and the gene fragment to be integrated (upstream homologous arm-target gene-downstream homologous arm). Using the primer design software primer5, the upstream and downstream sequences of the gene to be knocked out or the site to be integrated were used as the template to design the primers for the amplification of the upstream and downstream homologous arms (amplification product length: about 400-500 bp); the gene to be integrated was used as the template to design the primers for the amplification of the integrated gene. After amplifying the upstream and downstream homologous arms and the target gene fragment by PCR, respectively, the recombinant fragment was prepared by overlap PCR. The DNA polymerases used in PCR were purchased from TaKaRa, including high-fidelity PrimeSTAR HS DNA Polymerase and Ex.taq DNA Polymerase for generating sticky-end PCR products. The PCR systems and methods are shown in the following tables:

| PCR amplification system with HS enzyme | |
|---|---|
| Component | Volume (50 μL) |
| DNA template | 1 μL |
| Forward primer (10 μmol/L) | 2 μL |
| Reverse primer (10 μmol/L) | 2 μL |
| dNTP mixture (10 mmol/L) | 4 μL |
| 5 × Buffer | 10 μL |
| HS enzyme (5 U/μL) | 0.5 μL |
| $ddH_2O$ | 30.5 μL |

The colony PCR system is shown in the following table: PCR amplification system with Ex.taq enzyme

| PCR amplification system with Ex. taq enzyme | |
|---|---|
| Component | Volume (15 μL) |
| DNA template | 1 μL |
| Forward primer (10 μmol/L) | 0.5 μL |
| Reverse primer (10 μmol/L) | 0.5 μL |
| 2 × Rapid Taq Master Mix | 7.5 μL |
| $ddH_2O$ | 6.5 μL |
| DNA template | 1 μL |

The overlap PCR system is shown in the following table:

| Overlap PCR amplification system with HS enzyme | |
|---|---|
| Component | Volume (50 μL) |
| Template | 1 μL |
| Forward primer for the upstream homologous arm (10 μmol/L) | 2 μL |
| Reverse primer for the downstream homologous arm (10 μmol/L) | 2 μL |
| dNTP mixture (10 mmol/L) | 4 μL |
| 5 × Buffer | 10 μL |
| HS enzyme (5 U/μL) | 0.5 μL |
| $ddH_2O$ | 30.5 μL |

Note:
The template was composed of equal moles of amplified fragments of the upstream homologous arm and the downstream homologous arm and the target gene, and the total amount was less than 10 ng.

Note: The template was composed of equal moles of amplified fragments of the upstream homologous arm and the downstream homologous arm and the target gene, and the total amount was less than 10 ng.

| Overlap PCR amplification system with Ex. taq enzyme | |
|---|---|
| Component | Volume (50 μL) |
| Template | 2 μL |
| Forward primer for the upstream homologous arm (10 μmol/L) | 1 μL |
| Reverse primer for the downstream homologous arm (10 μmol/L) | 1 μL |
| dNTP mixture (10 mmol/L) | 4 μL |
| 10 × Buffer | 5 μL |
| Ex. taq enzyme (5 U/μL) | 0.25 μL |
| $ddH_2O$ | 36.75 μL |

Note:
The template was composed of equal moles of amplified fragments of the upstream homologous arm and the downstream homologous arm and the target gene, and the total amount was less than 10 ng.

Note: The template was composed of equal moles of amplified fragments of the upstream homologous arm and the downstream homologous arm and the target gene, and the total amount was less than 10 ng.

PCR reaction conditions: pre-denaturation at 95° C. for 5 min; 30 cycles of denaturation at 98° C. for 10 s, annealing at (Tm-3/5) ° C. for 15 s, extension at 72° C. (enzyme activity: about 1 minute per kb); and a final extension at 72° C. for 10 min; hold at 4° C.

1.3 Transformation of Plasmid and Recombinant DNA Fragment 1.3.1 Transformation of pREDCas9

The pREDCas9 plasmid was electro-transformed into the electro-transformation competent cells of W3110 by electro-transformation. The cells were recovered and cultured and spread on LB plates containing spectinomycin, and cultured at 32° C. overnight. Single colonies grown on the plates with the antibiotic were subjected to colony PCR with identification primers to screen positive recombinants.

1.3.2 Preparation of Electro-Transformation Competent Cells of the Target Strain Containing pREDCas9

The strain was cultured at 32° C. until the culture reached an OD600 of from 0.1 to 0.2, and then 0.1 M IPTG was added (to a final concentration of 0.1 mM). The culture was continued until OD600 value reached from 0.6 to 0.7. The obtained cells were used for the preparation of competent cells. The purpose of adding IPTG is to induce the expression of the recombinase on the pREDCas9 plasmid. The medium and preparation process required for the preparation of the competent cells refer to conventional standard operations.

1.3.3 Transformation of pGRB and Recombinant DNA Fragment

The pGRB plasmid and the donor DNA fragment were simultaneously electro-transformed into the electro-transformation competent cells containing pREDCas9. After electro-transformation, the cells were recovered and cultured and spread on LB plates containing ampicillin and spectinomycin, and cultured at 32° C. overnight. Colony PCR verification was performed by using the forward primer for the upstream homologous arm and the reverse primer for the downstream homologous arm, or by using specifically designed primers for identification, to screen positive recombinants and the recombinant bacteria were preserved.

1.4 Elimination of Plasmid 1.4.1 Elimination of Plasmid pGRB

The positive recombinants were cultured overnight in LB medium containing 0.2% arabinose, and after appropriate dilution, they were spread on LB plates containing spectinomycin, and cultured at 32° C. overnight. The recombinants were then inoculated into LB plates containing ampicillin and spectinomycin, respectively, and single colonies that did not grow on the plate containing ampicillin but grew on the plate containing spectinomycin were picked and preserved.

1.4.2 Elimination of Plasmid pREDCas9

The positive recombinants were transferred to LB liquid medium without antibiotics, cultured overnight at 42° C., and spread on LB plates without antibiotics after appropriate dilution, and cultured at 37° C. overnight. The recombinants were then inoculated into LB plates containing spectinomycin and without antibiotics, respectively, single colonies that did not grow on the plate with spectinomycin but grew on the LB plate without antibiotics were picked and preserved.

2. Construction of Engineered L-Tryptophan-Producing *E. coli* Strain TRP 05

2.1 Synthesis of ywkB Gene (1) Using *E. coli* W3110 genome as the template, PCR was performed with the primers for the upstream homologous arm (yeep-up-S, yeep-up-A) and the primers for the downstream homologous arm (yeep-down-S, yeep-down-A) designed at both ends of the yeep pseudogene to amplify the upstream and downstream homologous arms of the yeep pseudogene.

(2) The PCR primers (ywkB-S, ywkB-A) were designed according to the gene sequence of the putative metabolite transporter ywkB of *Bacillus subtilis* (*Bacillus subtilis* subsp. *subtilis* str. 168) published in GENBANK, and the sequence of BBa_j23106 promoter was designed in the forward primer for the ywkB gene and its fragment was amplified with HS enzyme.

(3) The amplified fragment obtained in steps (1) and (2) were used as the templates to obtain the integrated fragment of the BBa_j23106-ywkB gene by overlap PCR, and the fragment was composed of the upstream homologous arm of the yeep gene, the downstream homologous arm of the yeep gene, the BBa_j23106 promoter fragment and the ywkB gene fragment.

2.2 Integration of the ywkB Gene (1) Construction of pGRB-yeep: plasmid pGRB containing the target sequence was prepared according to the method described in section 1.1, specifically, primers, pGRB-yeep-S and pGRB-yeep-A, were designed according to the method of section 1.1.2, and then the DNA fragment containing the target sequence was obtained by annealing; the plasmid pGRB was linearized according to the method of section 1.1.3, and then plasmid pGRB-yeep containing the target sequence was prepared according to the method of section 1.1.4;

(2) preparation of competent cells of *E. coli* TRP 03;

(3) Acquisition of *E. coli* strain TRP 05: according to the method described in section 1.3, positive clones were screened after the pREDCas9 plasmid was transformed into *E. coli* TRP 03, and then the competent cells of *E. coli* TRP 03 containing the pREDCas9 plasmid was prepared, electro-transformed with the plasmid pGRB-yeep and the recombinant DNA fragments prepared in step (3) in section 2.1; colony PCR verification was performed after 12-16 hours of plate culture, positive recombinants were screeded and preserved; according to the method described in section 1.4, plasmid pGRB-yeep and plasmid pREDCas9 were eliminated, respectively, and finally the *E. coli* strain TRP 05 was screened through PCR identification and stored at −80° C.

The electropherogram of the construction of the BBa_j23106 ywkB gene integration fragment and the PCR verification of the positive strain are shown in FIG. 2, wherein, the length of the upstream homologous arm is 512 bp, the length of the downstream homologous arm is 513 bp, the length of the BBa_j23106 ywkB gene fragment is 1040 bp, and the total length of the BBa_j23106 ywkB gene integration fragment is 2065 bp. In the PCR verification, the length of the PCR amplified fragment of the positive bacteria was 2065 bp, and the length of the PCR amplified fragment of the original bacteria was 1396 bp.

3. The primers used in the strain improvement are shown in the following table:

| Primer | Sequence (5'-3') | SEQ ID NO: |
|---|---|---|
| yeep-up-S | GGTCAGGAGGTAAC TTATCAGCG | 4 |
| yeep-up-A | CTGCTAGCACTATA CCTAGGACTGAGCT AGCCGTAAAATGGC AGGGCTCCGTTTT | 5 |
| ywkB-S | AGGTATAGTGCTAG CAGGAAACAGACCT TGAGCATCTTAGAT ATCTTAATCCTCC | 6 |
| ywkB-A | AAATCCAGTTCAGC AAAAAGCTCCCTT AAAGGG | 7 |

-continued

| Primer | Sequence (5'-3') | SEQ ID NO: |
|---|---|---|
| yeep-down-S | TTTTTGCTGAACTG GATTTTCTTC TGAACCTGT | 8 |
| yeep-down-A | ACGATGTCAGCAG CCAGCA | 9 |
| pGRB-yeep-S | AGTCCTAGGTATA ATACTAGTACAGA ATATTCGCGAAAA AAGTTTTAG AGCTAGAA | 10 |
| pGRB-yeep-A | TTCTAGCTCTAAA ACTTTTTTCGCGA A TATTCTGTACT AGTATTATACCTA GGACT | 11 |

Example 2: Shake Flask Fermentation of Genetically Engineered *Escherichia coli* for the Production of L-Tryptophan A specific operation of using genetically engineered *Escherichia coli* to produce L-tryptophan by shake flask fermentation was as follows:

slant culture: inoculating the bacterial strain preserved at −80° C. onto an activated slant using streak method, culturing at 37° C. for 12 h and passaged once;

shake flask seed culture: scraping a ring of seeds on the slant with an inoculating loop and inoculating into a 500 mL conical flask containing 30 mL of seed medium, sealing the conical flask with nine layers of gauze, and culturing at 37° C. and 200 rpm for 8-10 h;

shake flask fermentation culture: inoculating the seed culture at the concentration of 10-15% (v/v) into a 500 mL conical flask containing fermentation medium (final volume: 30 mL), sealing the conical flask with nine layers of gauze, culturing at 37° C. and 200 r/min in a shaking table, during the fermentation, adding ammonia water to maintain pH at 7.0-7.2; adding 60% (m/v) glucose solution to maintain fermentation (with phenol red as indicator, when the color of the fermentation broth no longer changes, it is regarded as lack of glucose, adding 1-2 mL of 60% (m/v) glucose solution to make the glucose concentration in the fermentation broth the initial value of 20-40 g/L); the fermentation period lasting for 22-26 h.

Determination of L-tryptophan concentration in fermentation broth: 1 mL of fermentation broth was collected, centrifuged at 13,000 rpm for 1 min, and the supernatant was collected; the collected supernatant was diluted (to 0.1-0.5 g/L) with deionized water, filtered through a 0.22 un micropore, and the L-tryptophan concentration was determined by liquid chromatography; the chromatographic conditions were as follows: chromatographic column: Kromasil C18 column (250 mm×460 mm, 5 μm), mobile phase: 10% acetonitrile solution, flow rate: 1.0 mL/min, column temperature: 40° C., detection wavelength: 278 nm, injection volume: 20 μL, and the appearance time of the main peak was about 3.5 min; the concentration of L-tryptophan in the fermentation broth was calculated from its peak area according to a standard curve;

Plotting a standard curve of L-tryptophan: solutions with L-tryptophan concentrations of 0.1 g/L, 0.3 g/L, 0.5 g/L, 0.6 g/L and 1 g/L were subjected to the above liquid chromatography to obtain the peak areas corresponding to the L-tryptophan concentrations and the peak area was plotted against the concentration of L-tryptophan to generate the standard curve, as shown in FIG. 3.

Components of activated slant medium: 1-3 g/L glucose, 5-10 g/L tryptone, 5-10 g/L beef extract, 2-5 g/L yeast extract, 2-5 g/L NaCl, 15-30 g/L agar, the residual is water, pH 7.0-7.2, sterilized in an autoclave at 121° C. for 20 min.

Components of seed medium: 20-40 g/L glucose, 1-5 g/L $(NH_4)_2SO_4$, 1-5 g/L $KH_2PO_4$, 0.5-2 g/L $MgSO_4{\cdot}7H_2$, 2-5 g/L yeast extract, 1-3 mg/L $FeSO_4{\cdot}7H_2O$, 1-3 mg/L $MnSO_4{\cdot}H_2O$, 0.1-0.5 mg/L $V_H$, 0.5-1.0 mg/L $V_{B1}$, 1-3 ml/L trace element mixture, 15-30 g/L phenol red, the residual is water, pH 7.0-7.2, sterilized in an autoclave at 115° C. for 15 min.

Components of fermentation medium: 20-40 g/L glucose, 2-6 g/L $(NH_4)_2SO_4$, 1-5 g/L $KH_2PO_4$, 0.5-2 g/L $MgSO_4{\cdot}7H_2O$, 1-5 g/L yeast extract, 30-60 mg/L $FeSO_4{\cdot}7H_2O$, 1-5 mg/L $MnSO_4{\cdot}7H_2O$, 0.1-0.5 mg/L $V_H$, 0.5-1.0 mg/L $V_{B1}$, 1-3 ml/L trace element mixture, 15-30 g/L phenol red, the residual is water, pH 7.0-7.2, sterilized in an autoclave at 115° C. for 15 min.

Components of the trace element mixture: 2.5 g/L $Na_2MoO_4{\cdot}2H_2O$, 2.5 g/L $AlCl_3{\cdot}6H_2O$, 2.5 g/L $NiSO_4{\cdot}6H_2O$, 1.75 g/L $CoCl_2{\cdot}6H_2O$, 10 g/L $CaCl_2{\cdot}2H_2O$, 0.5 g/L $ZnSO_4{\cdot}7H_2O$, 0.25 g/L $CuCl_2{\cdot}2H_2O$, 0.125 g/L $H_3BO_3$.

Figure 4:
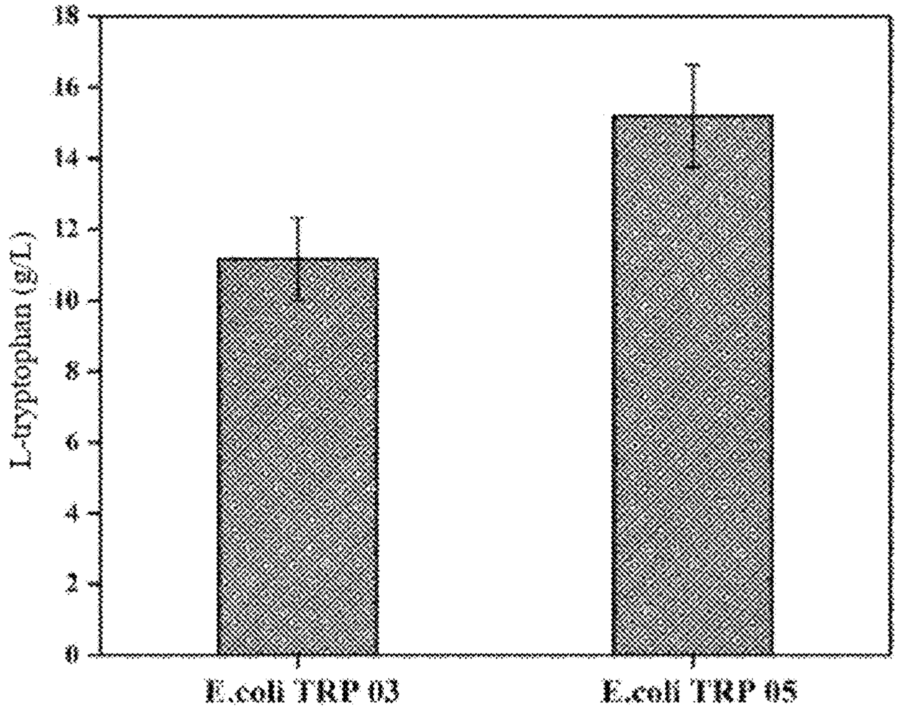
FIG. 4 shows the yields of L-tryptophan by shake flask fermentation.

The engineered L-tryptophan-producing *E. coli* strain TRP 05 constructed above was used for shake flask fermentation, and the engineered L-tryptophan-producing *E. coli* strain TRP 03 preserved in the Metabolic Engineering Laboratory of Tianjin University of Science and Technology was used as a control for the same shake flask fermentation. The experimental results are shown in FIG. 4. The engineered L-tryptophan-producing *E. coli* strain TRP 03 accumulated L-tryptophan up to 11.2 g/L, whereas *E. coli* TRP 05 accumulated L-tryptophan up to 15.2 g/L, which was 35% higher than the control strain.

The invention claimed is:

1. A method for constructing a genetically engineered bacterial strain comprising a step of integrating a ywkB gene into the yeep pseudogene locus of an *Escherichia coli* (*E. coli*) host strain which produces L-tryptophan, wherein the ywkB gene encodes the amino acid sequence of SEQ ID NO: 2, thereby producing a genetically-engineered bacterial strain which produces a higher yield of L-tryptophan than the *E. coli* host strain.

2. The method according to claim 1, wherein the integration step comprises integrating the ywkB gene into the yeep pseudogene locus by means of CRISPR-Cas9 gene editing.

3. The method according to claim 2, wherein the means of CRISPR-Cas9 gene editing comprises the following steps:

(1) synthesizing a donor sequence for integration, the donor sequence comprising: an upstream homologous arm fragment of the yeep pseudogene, the BBa_j23106 promoter of SEQ ID NO: 3, the ywkB gene, and a downstream homologous arm fragment of the yeep pseudogene, wherein the upstream and downstream homologous arm fragments of the yeep pseudogene are homologous to sequences comprised in the yeep pseudogene;

(2) integrating the donor sequence into the yeep pseudogene locus of the *E. coli* host strain using a CRISPR/Cas9 gene editing system.

4. The method according to claim 1, wherein the ywkB gene sequence encoding the amino acid sequence of SEQ ID NO: 2 is derived from *Bacillus subtilis*.

* * * * *

SEQUENCE LISTING

```
<160> NUMBER OF SEQ ID NOS: 11

<210> SEQ ID NO 1
<211> LENGTH: 993
<212> TYPE: DNA
<213> ORGANISM: Bacillus subtilis subsp. subtilis 168

<400> SEQUENCE: 1

ttgagcatct tagatatctt aatcctcctg gcgccgatct tctttgttat cgtgctgggt     60
```

-continued

```
tggtttgcag gacattttgg aagttatgat gccaagtcgg caaaaggggt aagtacgtta    120

gtaacgaaat acgcacttcc agctcacttt atcgctggta ttttgacaac ttccagaagt    180

gaatttttat cacaagtacc tttaatgatt tctttaatta ttgggattgt tggtttctat    240

atcatcattc ttttggtttg cagatttata ttcaagtatg atttaacgaa ctcatctgta    300

ttttctttga actctgcaca gccgacattc gcatttatgg gtatcccggt attgggaagc    360

ttattcggag cgaatgaagt tgcgattccg atcgcggtca caggtatcgt ggttaacgcg    420

attcttgatc cgctcgcgat cattatcgct actgttggtg agtcttctaa gaaaaacgaa    480

gagagtggcg acagcttctg gaagatgaca ggaaaatcaa tcctgcatgg tctttgtgag    540

ccgcttgcag ctgctccgtt aatcagtatg atcttggtgc tggttttcaa tttcactctt    600

cctgagctgg gtgttaaaat gcttgatcag cttggaagca caacatctgg tgttgctctc    660

ttcgctgttg gtgttaccgt tggtattcgt aaaattaaac tcagtatgcc ggctatcggt    720

attgcgttac taaaagttgc ggttcagcct gcgttaatgt tcctgattgc tcttgctatc    780

ggacttccag ctgaccaaac aacaaaagca atccttcttg ttgcattccc tggttctgcc    840

gttgcagcca tgattgcgac tcgtttcgag aaacaagaag aagaaactgc aactgcgttt    900

gtggtcagtg cgattctgtc attgatttca cttccaatca ttatcgcgct tactgcgtaa    960

caaaaaaagc tccctttaag ggagcttttt gct                                 993
```

```
<210> SEQ ID NO 2
<211> LENGTH: 319
<212> TYPE: PRT
<213> ORGANISM: Bacillus subtilis subsp. subtilis 168

<400> SEQUENCE: 2

Met Ser Ile Leu Asp Ile Leu Ile Leu Leu Ala Pro Ile Phe Phe Val
1               5                   10                  15

Ile Val Leu Gly Trp Phe Ala Gly His Phe Gly Ser Tyr Asp Ala Lys
            20                  25                  30

Ser Ala Lys Gly Val Ser Thr Leu Val Thr Lys Tyr Ala Leu Pro Ala
        35                  40                  45

His Phe Ile Ala Gly Ile Leu Thr Thr Ser Arg Ser Glu Phe Leu Ser
    50                  55                  60

Gln Val Pro Leu Met Ile Ser Leu Ile Ile Gly Ile Val Gly Phe Tyr
65                  70                  75                  80

Ile Ile Ile Leu Leu Val Cys Arg Phe Ile Phe Lys Tyr Asp Leu Thr
                85                  90                  95

Asn Ser Ser Val Phe Ser Leu Asn Ser Ala Gln Pro Thr Phe Ala Phe
            100                 105                 110

Met Gly Ile Pro Val Leu Gly Ser Leu Phe Gly Ala Asn Glu Val Ala
        115                 120                 125

Ile Pro Ile Ala Val Thr Gly Ile Val Val Asn Ala Ile Leu Asp Pro
    130                 135                 140

Leu Ala Ile Ile Ile Ala Thr Val Gly Glu Ser Ser Lys Lys Asn Glu
145                 150                 155                 160

Glu Ser Gly Asp Ser Phe Trp Lys Met Thr Gly Lys Ser Ile Leu His
                165                 170                 175

Gly Leu Cys Glu Pro Leu Ala Ala Ala Pro Leu Ile Ser Met Ile Leu
            180                 185                 190

Val Leu Val Phe Asn Phe Thr Leu Pro Glu Leu Gly Val Lys Met Leu
        195                 200                 205
```

```
Asp Gln Leu Gly Ser Thr Thr Ser Gly Val Ala Leu Phe Ala Val Gly
    210                 215                 220

Val Thr Val Gly Ile Arg Lys Ile Lys Leu Ser Met Pro Ala Ile Gly
225                 230                 235                 240

Ile Ala Leu Leu Lys Val Ala Val Gln Pro Ala Leu Met Phe Leu Ile
                245                 250                 255

Ala Leu Ala Ile Gly Leu Pro Ala Asp Gln Thr Thr Lys Ala Ile Leu
            260                 265                 270

Leu Val Ala Phe Pro Gly Ser Ala Val Ala Ala Met Ile Ala Thr Arg
        275                 280                 285

Phe Glu Lys Gln Glu Glu Glu Thr Ala Thr Ala Phe Val Val Ser Ala
    290                 295                 300

Ile Leu Ser Leu Ile Ser Leu Pro Ile Ile Ile Ala Leu Thr Ala
305                 310                 315


<210> SEQ ID NO 3
<211> LENGTH: 47
<212> TYPE: DNA
<213> ORGANISM: Artificial Sequence
<220> FEATURE:
<223> OTHER INFORMATION: Synthesized

<400> SEQUENCE: 3

tttacggcta gctcagtcct aggtatagtg ctagcaggaa acagacc                   47


<210> SEQ ID NO 4
<211> LENGTH: 23
<212> TYPE: DNA
<213> ORGANISM: Artificial Sequence
<220> FEATURE:
<223> OTHER INFORMATION: Synthesized

<400> SEQUENCE: 4

ggtcaggagg taacttatca gcg                                             23


<210> SEQ ID NO 5
<211> LENGTH: 55
<212> TYPE: DNA
<213> ORGANISM: Artificial Sequence
<220> FEATURE:
<223> OTHER INFORMATION: Synthesized

<400> SEQUENCE: 5

ctgctagcac tatacctagg actgagctag ccgtaaaatg gcagggctcc gtttt          55


<210> SEQ ID NO 6
<211> LENGTH: 55
<212> TYPE: DNA
<213> ORGANISM: Artificial Sequence
<220> FEATURE:
<223> OTHER INFORMATION: Synthesized

<400> SEQUENCE: 6

aggtatagtg ctagcaggaa acagaccttg agcatcttag atatcttaat cctcc          55


<210> SEQ ID NO 7
<211> LENGTH: 33
<212> TYPE: DNA
<213> ORGANISM: Artificial Sequence
<220> FEATURE:
<223> OTHER INFORMATION: Synthesized

<400> SEQUENCE: 7
```

-continued

```
aaatccagtt cagcaaaaag ctcccttaaa ggg                              33


<210> SEQ ID NO 8
<211> LENGTH: 33
<212> TYPE: DNA
<213> ORGANISM: Artificial Sequence
<220> FEATURE:
<223> OTHER INFORMATION: Synthesized

<400> SEQUENCE: 8

tttttgctga actggatttt cttctgaacc tgt                              33


<210> SEQ ID NO 9
<211> LENGTH: 19
<212> TYPE: DNA
<213> ORGANISM: Artificial Sequence
<220> FEATURE:
<223> OTHER INFORMATION: Synthesized

<400> SEQUENCE: 9

acgatgtcag cagccagca                                              19


<210> SEQ ID NO 10
<211> LENGTH: 56
<212> TYPE: DNA
<213> ORGANISM: Artificial Sequence
<220> FEATURE:
<223> OTHER INFORMATION: Synthesized

<400> SEQUENCE: 10

agtcctaggt ataatactag tacagaatat tcgcgaaaaa agttttagag ctagaa     56


<210> SEQ ID NO 11
<211> LENGTH: 56
<212> TYPE: DNA
<213> ORGANISM: Artificial Sequence
<220> FEATURE:
<223> OTHER INFORMATION: Synthesized

<400> SEQUENCE: 11

ttctagctct aaaacttttt tcgcgaatat tctgtactag tattatacct aggact     56
```